(12) United States Patent
Zhang et al.

(10) Patent No.: US 9,409,769 B2
(45) Date of Patent: Aug. 9, 2016

(54) NANOSTRUCTURED DEVICES FOR DETECTING AND ANALYZING BIOMOLECULES

(75) Inventors: An-Ping Zhang, Rexford, NY (US); Anthony John Murray, Lebanon, NJ (US); Rui Chen, Clifton Park, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 2368 days.

(21) Appl. No.: 11/947,834

(22) Filed: Nov. 30, 2007

(65) Prior Publication Data

US 2016/0202254 A1    Jul. 14, 2016

(51) Int. Cl.
*G01N 27/327* (2006.01)
*B82Y 15/00* (2011.01)
*G01N 27/30* (2006.01)

(52) U.S. Cl.
CPC .............. *B82Y 15/00* (2013.01); *G01N 27/327* (2013.01)

(58) Field of Classification Search
CPC . G01N 27/3271; G01N 27/327; G01N 27/30; G01N 27/28; G01N 27/26; B82Y 15/00
USPC ........................ 422/82.01, 68.1, 50
See application file for complete search history.

(56) References Cited

U.S. PATENT DOCUMENTS

| 4,238,757 A | 12/1980 | Schenck |
| 6,331,493 B1 * | 12/2001 | Sharan .......................... 438/765 |
| 7,129,554 B2 | 10/2006 | Lieber et al. |

FOREIGN PATENT DOCUMENTS

WO    WO 2006119251 A2 * 11/2006   ............. B01D 61/00

OTHER PUBLICATIONS

Park et al., Block Copolymer Lithography: Periodic Arrays of ~ 10 Holes in 1 Square Centimeter, Science, vol. 276, May 30, 1997, 1401-1404.
Patolsky et al., "Nanowire-Based Nanoelectronic Devices in the Life Sciences", MRS Bulletin, vol. 32, Feb. 2007, 142-149.
Patolsky et al., "Nanowire-Based Biosensors", American Chemical Society (2006), 4261-4269.
Hahn et al., "Direct Ultrasensitive Electrical Detection of DNA and DNA Sequence Variations Using Nanowire Nanosensors", Nano Letters, (2004), vol. 4, No. 1, 51-54.

\* cited by examiner

*Primary Examiner* — Christine T Mui
(74) *Attorney, Agent, or Firm* — Fletcher Yoder, P.C.

(57) ABSTRACT

A biosensing FET device, comprising a plurality of nanostructured SOI channels, that is adapted to operate in solutions having a high ionic strength and provides improves sensitivity and detection. Generally, the biosensing device comprises an underlying substrate layer, an insulator and a semiconductor layer and a plurality of channels in the semiconductor layer comprising a plurality of whole or partially formed nanopores in the channels.

12 Claims, 12 Drawing Sheets

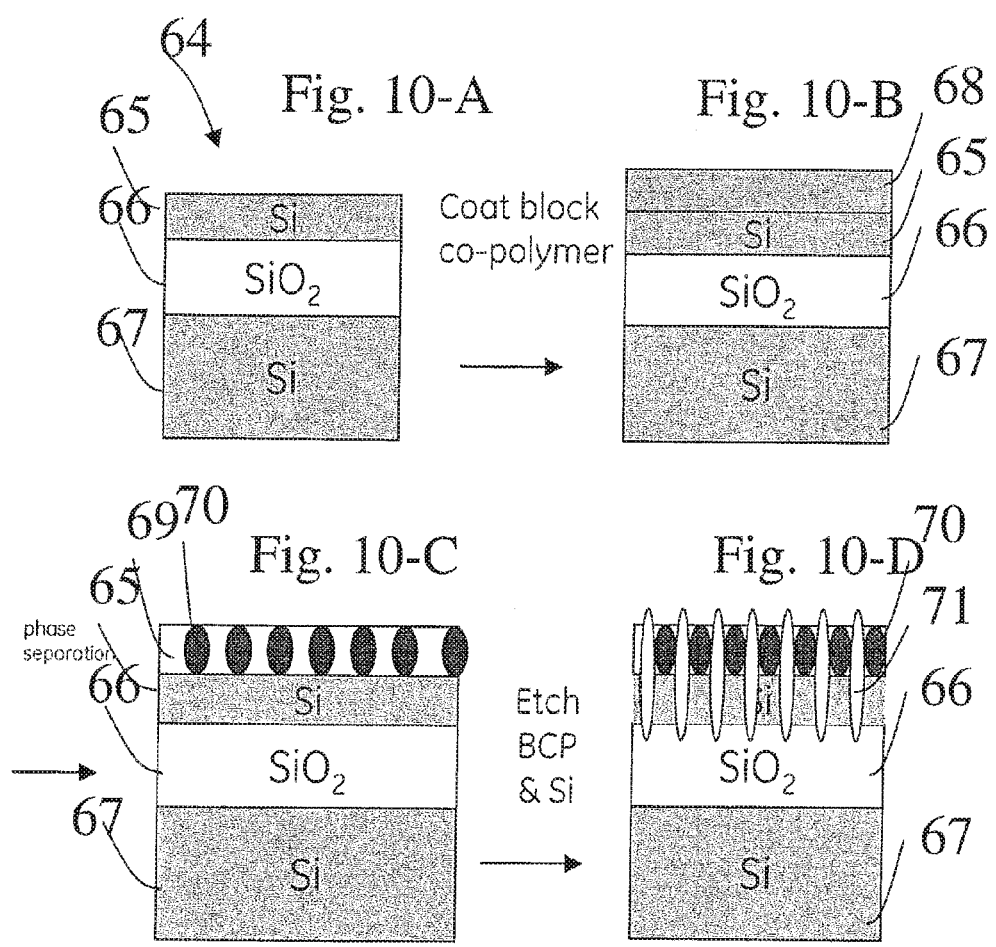

Fig. 10-E
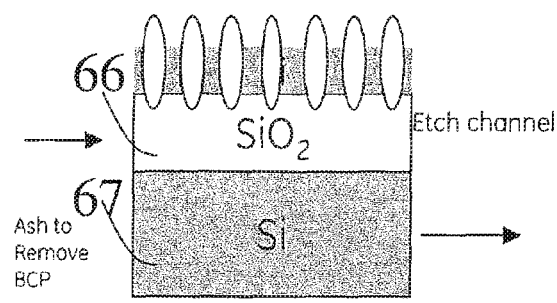
Fig. 10-F
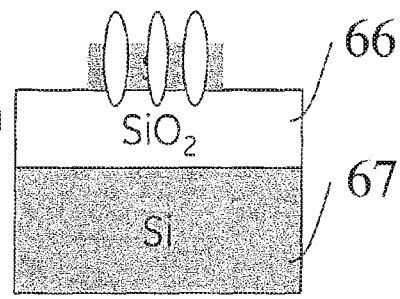
Fig. 10-G
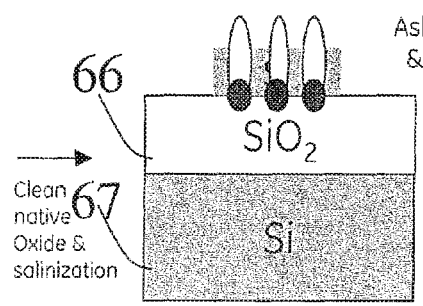
Fig. 10-H
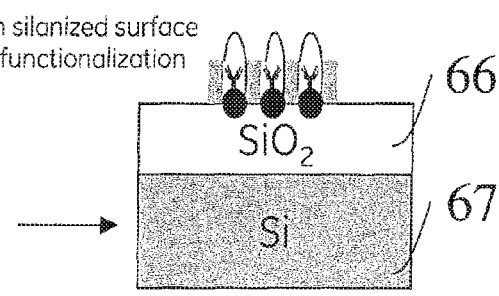

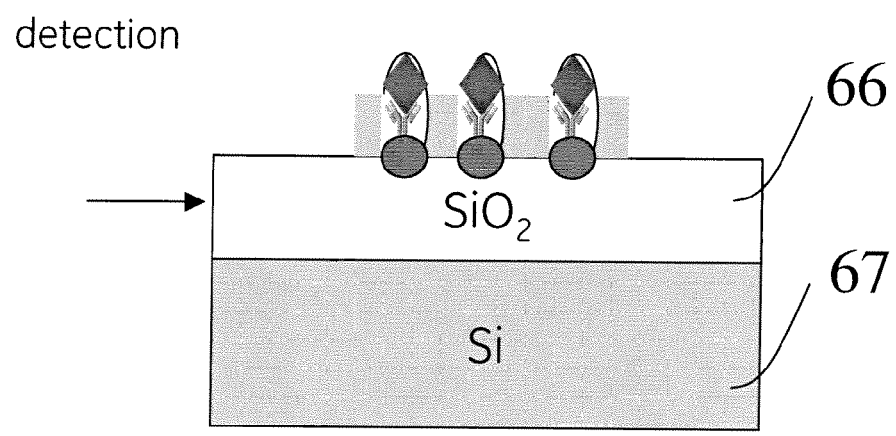
Fig. 10-I

NANOSTRUCTURED DEVICES FOR DETECTING AND ANALYZING BIOMOLECULES

BACKGROUND

The invention relates generally to nanostructured devices for detecting or analyzing biomolecules and their interactions.

Proteomics offers great potential for discovering biomarker patterns for earlier screening and detection of lethal and infectious diseases, systematic monitoring of physiological responses to drugs, and selecting the best treatment options for individual patients. For routine clinical use, an inexpensive, easy-to-use, multiplexed and high throughput protein analysis platform is needed, with high sensitivity and specificity for detection of low-abundance biomarkers in serum or other body fluids. There is also a need for high throughput and highly integrated sensor arrays for drug screening.

Nanostructured sensor arrays that use purely electrical detection, such as a field effect transistor (FET), fabricated with Si or other semiconductors, offer some of the desired characteristics. In such a device, a device channel of Si or other semiconductors is defined between two electrodes. The surface of the semiconductor channel or its oxide surface may be modified and covalently functionalized with antibodies or other receptor ligands for quantitative biorecognition. The binding of protein or other biomolecules induces net charge change, or change in dipole moment and binding-induced dipoles or modification of energy distribution and/or density of surface states. These binding events can change surface potential of the FET device and therefore modulate the conductance of the semiconductor channel. A small voltage or current, small enough not to disturb biomolecule interactions, is applied between two electrodes, and the change in conductance of the device channel is related and calibrated to the analyte concentration in a solution. When the device channel is reduced to nanoscale, the detection limit can be significantly reduced due to increased surface-to-volume ratio. Further, the response time can also be reduced due to favorable mass transport at low analyte concentrations due to small binding capacity of the small sensing surface. The ultralow detection limit of the nano-FET sensor at low ionic strength solutions has been recently demonstrated.

However, these devices may be rendered ineffective due to the screening effect in higher ionic strength solutions. The Debye screening length is defined as the distance from the sensing surface where potential change can be detected by the sensing device. In a high ionic strength solution, the screening length is reduced by ions and thus, analytes present beyond the screening length cannot be detected. As shown in FIG. 1, the Debye screening length decreases with an increase in ionic strength, therefore the binding events may not be detectable in high ionic strength solutions. It would be desirable to provide a method and a device that would enable a nano-FET biosensor to operate at higher ionic strengths when physiological samples with high ionic strength are to be analyzed, such as analyzing protein biomarkers in serum or other body fluids.

The Debye-Huckel Theory is useful to better understand the issues associated with operating biosensing devices in higher ionic solutions. For example, assuming a perfect orientation of an immobilized antibody, FIG. 2 shows the interaction between an antigen and an antibody in a solution. The potential distribution as a function of distance away from the electrolyte-immuno FET interface with immobilized antibodies is shown for both high ionic strength and low ionic strength cases. It can be seen from FIG. 2 that the electrostatic potential decreases rapidly as the binding site moves away from the electrolyte/gate insulator interface. The Debye screening length, δ, can be simply defined, in this example, as the distance away from the electrolyte/gate insulator interface at which a charge redistribution can still be detected by the FET sensor. In the high ionic strength environment, the Debye length is extremely short due to charge screening of the analyte antigen by excess ions (or more precisely "counterions") present in solution. From the FET perspective, this charge screening effect makes it ineffective to detect charges induced by antigen/antibody interaction beyond the screening distance and therefore the anitigen molecule must come closer to the sensor surface in order for its intrinsic or induced charges to be detected. Beginning with a buffer solution with an ionic strength solution of 0.2M, for example, the calculated Debye length is approximately 1 nm, which is significantly shorter than the average length of an antibody molecule (~10 nm). Therefore the binding of antigen to the antibody receptor results in the redistribution of charges too distant to be detected by the FET sensor. However, in the absence of such excess charged species in solution, as in the case for low ionic strength situation, the screening effect by counterions is not as severe. The Debye length is much longer and the antigen molecule can be detected at a distance that is further away from the sensing surface. The overlapping of potentials in FIG. 2 in the low ionic strength case signifies a measurable effect with potentiometrically-operated immunoFET. The equation for Debye screening length in electrolytic solution is illustrated as:

$$\delta = \sqrt{\frac{\varepsilon K_B T}{8\pi e^2 I}}$$

where $K_B$ is the Boltzmann constant, T is temperature, e is the elementary charge ($1.6 \times 10^{-19}$ C), $\varepsilon$ is the dielectric constant, and I is the ionic strength which has the expression $$I = \frac{\sum_{1}^{i} n_i Z_i^2}{2}$$

where ni represents the concentration of the ith ionic species in the electrolytic solution and Zi is the charge of the ith species. The sum of the product of the concentration and charge of all ionic species gives an estimate of the ionic strength of the electrolytic solution. Since the Debye length varies as the inverse square root of the ionic strength, the sensing response depends on the ionic strength of the solution.

The nanoscale channel can increase surface-to-volume ratio of the device and therefore significantly lower the detection limit, but lithography tools that are expensive and lower throughput are required to define nanoscale patterns. It would also be desirable to increase surface-to-volume ratio of the channel without reducing the channel to nanoscale size, so larger channel size can be used to achieve the low detection limit and more conventional and inexpensive lithography tools can be used. It can significantly reduce the cost of device fabrication.

BRIEF DESCRIPTION

The invention generally relates to a semiconductor sensing device having a raised structure, referred to as device channel, wherein the device channel comprises one or more nanopores whole or partially formed in the raised structure on an underlying insulating layer on a substrate. The invention also generally relates to methods of making and using the sensing device that comprises nanopores formed in a silicon-on-insulator structure (SOI), such as a Si channel with nanopores. This nanopore structure physically brings binding sites of antibodies or other receptor molecules proximate to a sensing surface and enables the biosensor to operate at a higher ionic strength. In addition, the nanopores in the channels of the sensing device increase surface/volume ratio of the device, and enable lower detection limits and greater sensitivity at larger device channel size.

The devices and methods use nanostructured SOI channels to enable the sensor to operate in higher ionic strength solutions. In one embodiment, nanopores are formed in the device channel and stop at the underlying SiO2 layer. The antibodies or other receptor ligands can be selectively functionalized on the underlying SiO2 layer inside the nanopores. In another embodiment, a thin metal layer, such as Au or Ag, may be selectively deposited on the underlying SiO2 layer inside the nanopores by a lift-off process. Antibody or other receptor ligands can be selectively functionalized on the metal surface. The nanopores effectively locate the binding sites proximate to the sensing surface. The size and pitch of the nanopores may be controlled using block copolymer methods or other suitably controllable nanopatterning methods. In another embodiment the device comprises an underlying substrate layer, an insulator and a semiconductor layer and the one or more channels on the underlying insulator layer comprising one or more nanopores of varying depths in the channels.

An embodiment of the biosensing FET device, of the invention, having a sensing surface, generally comprises: a semiconductor layer comprising one or more channels having one or more nanopores in the channel; an insulator layer; and an underlying substrate layer.

In one or more of the embodiments, the channels may have a height and one or more of the nanopores has a depth in the channels, that is less than, equal to, and greater than, the height of one or more of the channels.

One or more of the embodiments may comprise nanopores that are functionalized. For example, the nanopores may have a depth that is greater than the height of one or more of the channels so that the nanopores extend through the top surface of, and partially into, the insulator layer, and wherein the nanopores have an inside surface, at least a portion of which is functionalized, that is partially in the semiconductor layer and partially in the insulator layer. Although not intended to be limiting, the all or part of the surface of the nanopores may functionalized, for example, with one or more binders. The nanopores in the semiconductor channel may be adapted to locate one or more binding sites proximate the sensing surface. As a non-limiting example, the device may be adapted to operate in solutions having an ionic strength that is equal to or less than 10 mM; wherein the nanopores are adapted to locate one or more of the binding sites less than or equal to 5 nm from the sensing surface. As another example, the device may be adapted to operate in solutions having an ionic strength that is equal to or less than 200 mM; and wherein the nanopores locate the binding sites less than or equal to 1 nm from the sensing surface. The channels may have a range of densities of nanopores such, as but not limited to, between $10^{10}$ to $10^{12}$ per $cm^{-2}$.

Any one or more of the embodiments of the biosensing device may be incorporated into a biosensing detector.

An embodiment of the method of the invention, of making a biosensing device, generally comprises the steps of: a) providing an underlying substrate layer; b) disposing an insulator on the substrate; c) disposing a semiconductor, having an exposed surface with one or more channels, on the insulator layer; and d) forming one or more nanopores in one or more of the channels; wherein the channels may have a density of nanopores between $10^{10}$ to $10^{12}$ per $cm^{-2}$. The nanopores may also be functionalized.

As a non-limiting example, the nanopores may be formed in the channels to achieve a density of nanopores between $4\times10^{10}$ to $2\times10^{11}$ per $cm^{-2}$ and wherein the nanopores have a pitch between 20 nm to 50 nm. One or more of the channels has a height and one or more of the nanopores has a depth that is less than, equal to, or greater than, the height of one or more of the channels.

The nanopores may be formed by, but not limited to, nanopatterning, such as, block copolymer lithography; wherein block copolymer lithography may comprise the steps of: (a) coating the semiconductor with a block copolymer capable of phase separating; (b) providing stimulus to form phase separated block copolymer; (c) etching the semiconductor layer to form one or more nanopores; and (d) removing at least a portion of the phase separated block copolymer. The block copolymer may comprise, but is not limited to, one or both of polystyrene-block-polybutadiene and polystyrene-block-polyisoprene.

One or more of the channels may have a height and one or more of the nanopores may have a depth that is equal to or greater than the height of one or more of the channels, so that the nanopores extend through the semiconductor layer and into the insulator layer; and wherein the nanopores may be silanized.

DRAWINGS

These and other features, aspects, and advantages of the present invention will become better understood when the following detailed description is read with reference to the accompanying drawings in which like characters represent like parts throughout the drawings, wherein:

FIGS. 10A to 10I illustrate embodiments of the steps for fabricating the biosensing device of the invention.

DETAILED DESCRIPTION

The present disclosure provides an embodiment of a biosensing device in which nanopores are etched into the channels of a nano-field effect transistor (FET) device. The nanopores are formed as described below by block copolymer nanolithography or by other nanopatterning techniques such as nanoimprint, soft lithography, or by e-beam lithography, etc. as described below.

Figure 3:
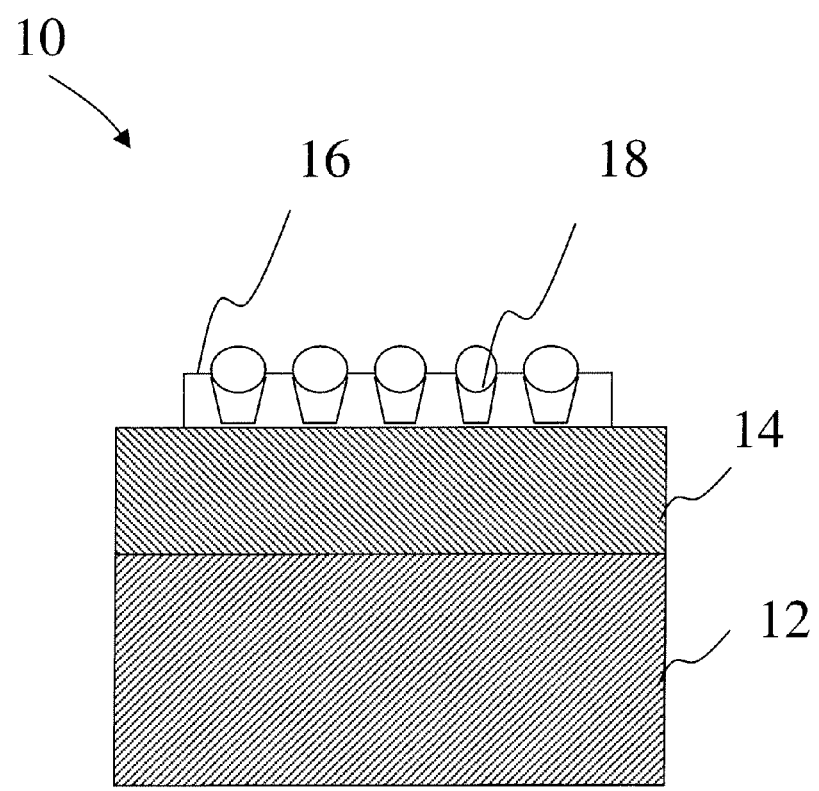
FIG. 3 illustrates an embodiment of a channel of a biosensing device in which the nanopores are formed by etching completely through the semiconductor layer.

Referring to the drawings, FIG. 3 shows a biosensing device 10 as one embodiment of the invention. The biosensing device comprises a substrate layer 12. The substrate layer may be made from a material such as silicon or glass. The biosensing device further comprises an insulator layer 14 on the top surface of the substrate. The insulator layer may be made from an insulating material, such as but not limited to, silicon oxide, silicon nitride, and the like. On the surface of the insulator layer 14 formed on the substrate layer 12, a semiconductor layer 16 is made available in the form of raised structures characterized by height, to form device channels with nanopores 18 on the insulator layer. An exemplary material used to make semiconductor layer includes silicon. The height of the semiconductor layer is generally uniform in a given biosensing device, and ranges from about 1 nm to about 1000 nm preferably 5 nm to 20 nm. Within the channels, nanopores 18 are present. The underlying insulating layer exposed inside nanopores, such as silicon oxide, is functionalized with binders, such as, but not limited to, antibodies or other receptor molecules or receptor ligands to provide binding sites, which are used for identification and quantifying of analytes. As used herein, a binder generally refers to molecules that have binding affinities either with themselves or more commonly with other molecules. Generally, the binder specifically binds to an analyte of interest. For example, such molecules include, but are not limited to, antigens, antibodies, affibodies, nanobodies, an enzyme, an enzyme substrate/inhibitor, aptamer and nucleic acids. This list is not exhaustive. Such binders may be used to functionalize one or more surfaces of the devices.

The biosensing device further comprises a source electrode and drain electrode. The biosensing device is useful in identifying and quantifying analytes such as, but not limited to, antigens, antibodies, nanobodies, affibodies, aptamers, nucleic acids, proteins, viruses and other chemical moieties.

Figure 1:
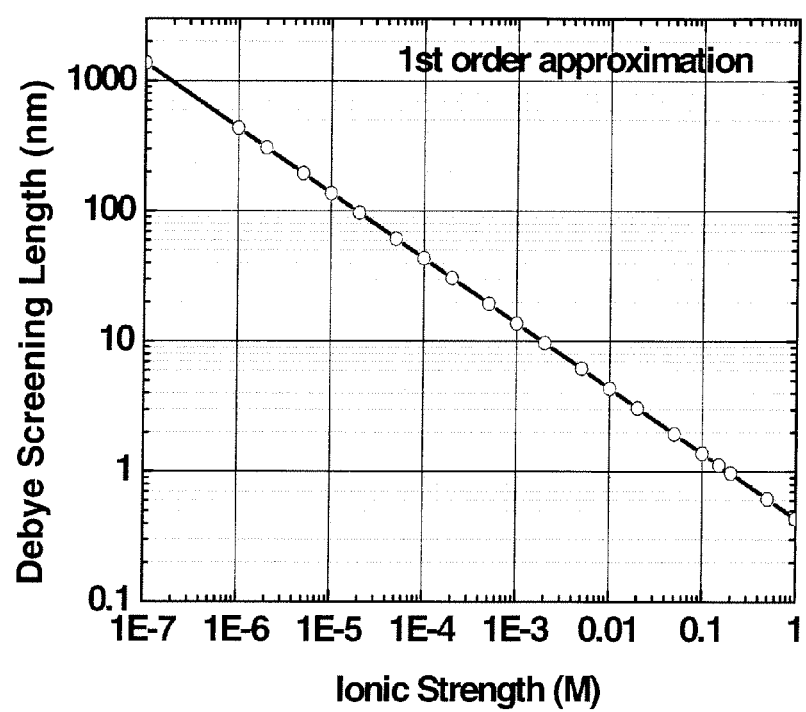
FIG. 1 is a graph illustrating a decrease in the Debye Screening Length as the ionic strength of an ionic solution increases, thus disabling a biosensing device from operating in a high ionic solution.
Figure 2:
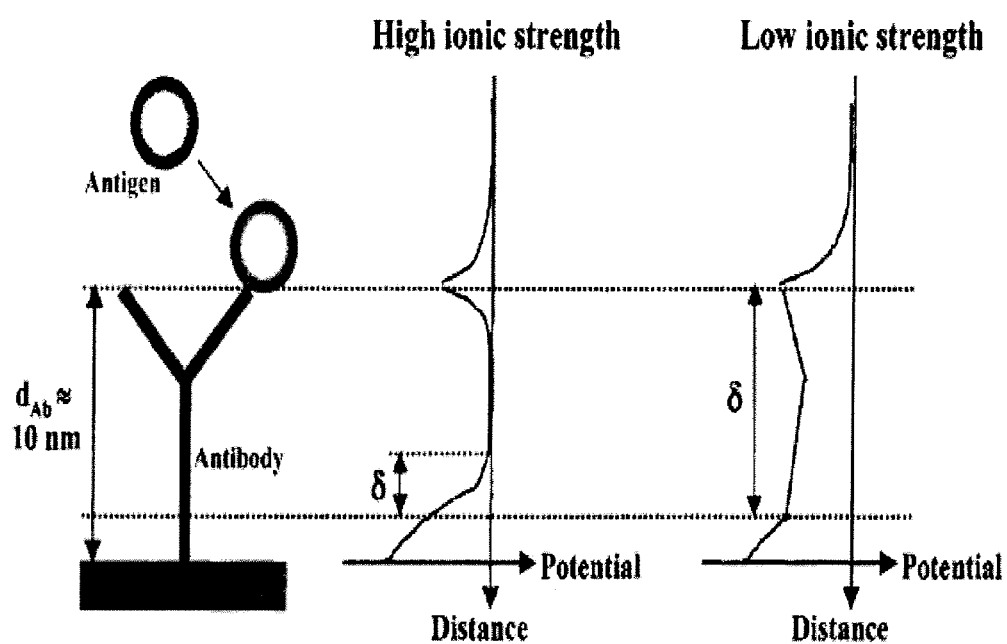
FIG. 2 is a graph illustrating the influence of solution ionic strength on the response of nano-FET sensor.

The presence of nanopores in the device channels locates the binding sites close to the sensing surface of the device. As a result, the charges, induced by the binding events at the binding sites, may be detected by the biosensing device, even in the presence of high ionic strength solutions. The presence of nanopores in the device channels also increases the surface-to-volume ratio of the device channel. This results in increased sensitivity towards the analytes to be detected. Thus, the biosensing device is useful for identifying and quantifying analytes in solution, including solutions having high ionic strength. The biosensing device reduces or eliminates the need for extensive desalting steps of the solution containing analytes before the detection. Further, with low detection limits, simple dilution by low ionic strength buffer can lower the ionic strength to a level allowing detection by the biosensing device of the invention. The presence of nanopores in the device channel also increases surface-to-volume ratio and therefore achieve very low detection limit even at large channel width. Thus expensive lithography steps can be avoided. As shown in FIG. 1, it can be seen that, for antibodies having an average size of approximately 10 nm, the nanowire sensor without nanopores can detect binding events in approximately 1 mM ionic solutions. If the presence of nanopores brings the binding sites to approximately 5 nm away from the sensing surface, the sensor can work in an approximately 10 mM ionic strength solutions. Similarly, with a 1 nm separation between binding sites and the sensing surface with nanopores, the nanowire sensor can operate in 200 mM ionic strength solutions.

Figure 4:
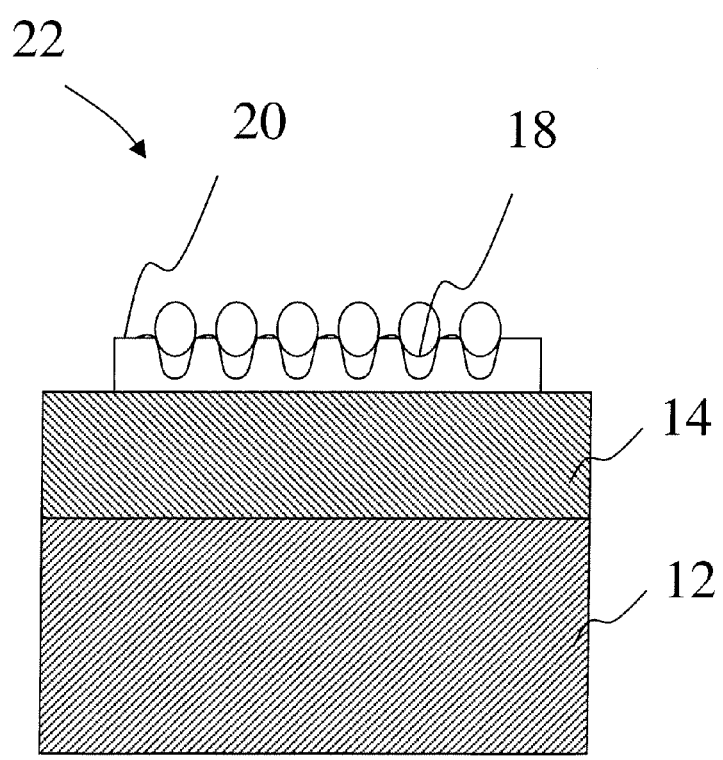
FIG. 4 illustrates an embodiment of a channel of a biosensing device in which the nanopores are partially etched through the semiconductor layer to form the nanopores having a depth that is less than the height of the channel.

FIG. 4 shows a biosensing device 22 with incompletely etched nanopores 18 in the semiconductor channel. The biosensing device comprises a substrate layer 12. The biosensing device further comprises an insulator layer 14 on the top surface of the substrate. On the surface of the insulator layer 14 formed on the substrate layer 12, a semiconductor layer 20 is made available in the form of raised structures characterized by height, to form device channels with nanopores 18 in the semiconductor layer. An exemplary material used to make semiconductor layer includes silicon. The height of the semiconductor layer is generally uniform in a given biosensing device, and ranges from about 1 nm to about 1000 nm preferably 5 nm to 20 nm. The nanopores 18 is incompletely etched in semiconductor layer 20. The presence of nanopores 18 can increase surface-to-volume ratio of the semiconductor channel and enhance single-to-noise ratio of the sensing device. Therefore the detection limit can be lowered and sensitivity of the biosensing device is improved. The exposed sensing surface of the semiconductor channel is functionalized with antibodies or other receptor molecules or receptor ligands to provide binding sites, which are used for identification and quantifying of analytes.

Figure 5:
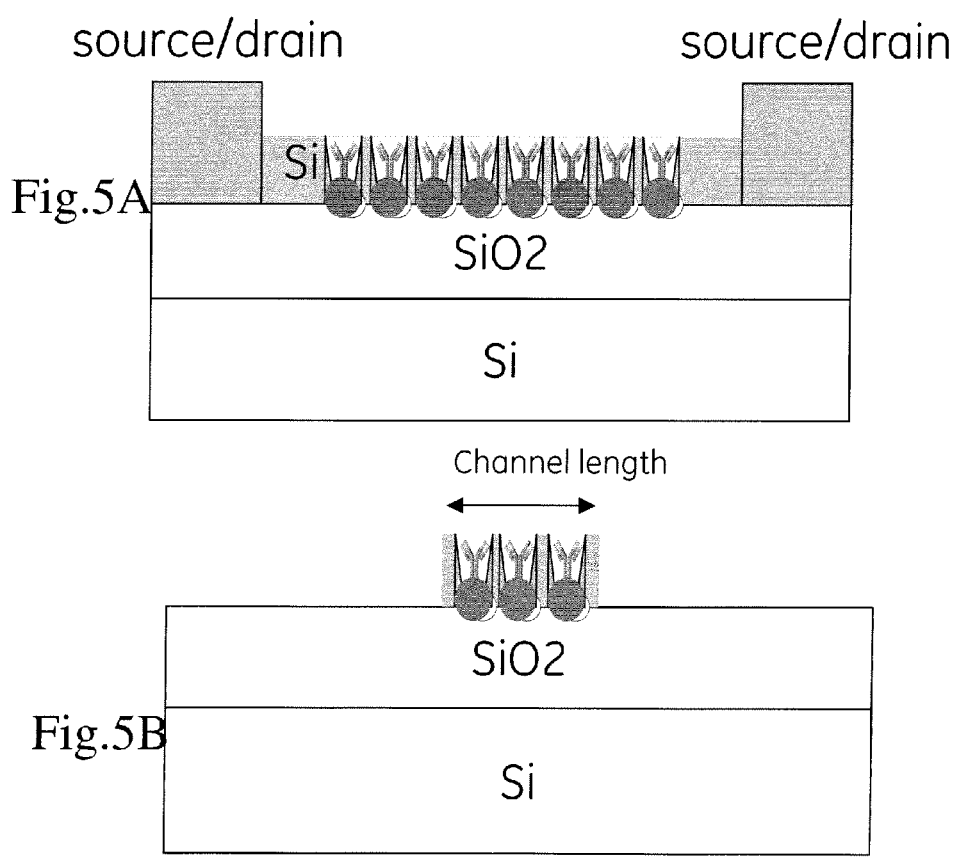
FIGS. 5A and 5B illustrate a channel with nanopores located therein having diameters of approximately 10-20 nm.
Figure 6:
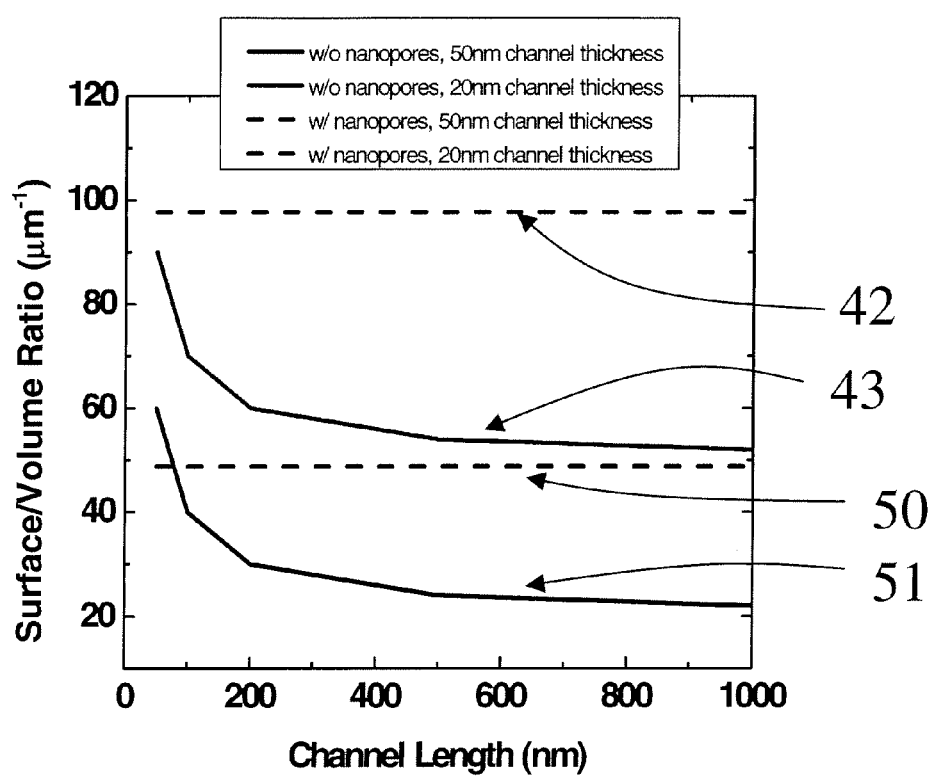
FIG. 6 is a diagram of Surface/Volume ratio vs. Channel length for channels shown in FIGS. 5A and 5B, with and without nanopores where the channel width is approximately 20 nm or 50 nm.

The nanopores in the device channel increase the surface-to-volume ratio and sensitivity at larger device channel width. FIG. 6 is a graph of the embodiments shown in FIGS. 5A and 5B illustrating the difference between channels with 20 nm thickness and channels with 50 nm thickness with and without nanopores. The diameter of the nanopores is 10 nm and the pitch is 20 nm. As seen in line 51, a channel with a 50 nm thickness without nanopores decreases in surface/volume ratio from 60 $\mu m^{-1}$ about 22 $\mu m^{-1}$ when the channel length increases from 50 nm to 1000 nm. While the same channel, as shown in line 50, with the same thickness of 50 nm channels with nanopores maintains surface/volume ratio of approximately 50 as the channel length increases from about 50 nm to 1000 nm.

Similarly FIG. 6 shows, in line 43, that a channel with 20 nm thickness without nanopores that the surface to volume ratio drops from about 90 $\mu m^{-1}$ to at a channel width of about 50 nm to a surface to volume ratio of about 52 $\mu m^{-1}$ for a channel width of up to 1000 nm. Comparatively, as shown in line 42, a channel with the same 20 nm length with nanosized pores remains at about 100 $\mu m^{-1}$ for its surface to volume ratio as the channel length increase from about 50 nm to up to 1000 nm. This illustrates that completely etched nanopores in the semiconductor channel increase surface-to-volume ratio and achieve high sensitivity for larger channel width. The density of nanopores is about $2.5 \times 10^{11}$ $cm^{-2}$ for 10 nm diameter nanopores with 20 nm pitch, which is comparable to the antibody density typically achieved on a Si/SiO2 surface ($10^{10} \sim 10^{12}$ $cm^{-2}$). Preferably the density is in the range of $4 \times 10^{10}$ to $2 \times 10^{11}$ $cm^{-2}$ corresponding to pitches of nanopores between 20 nm to 50 nm.

Figure 7A:
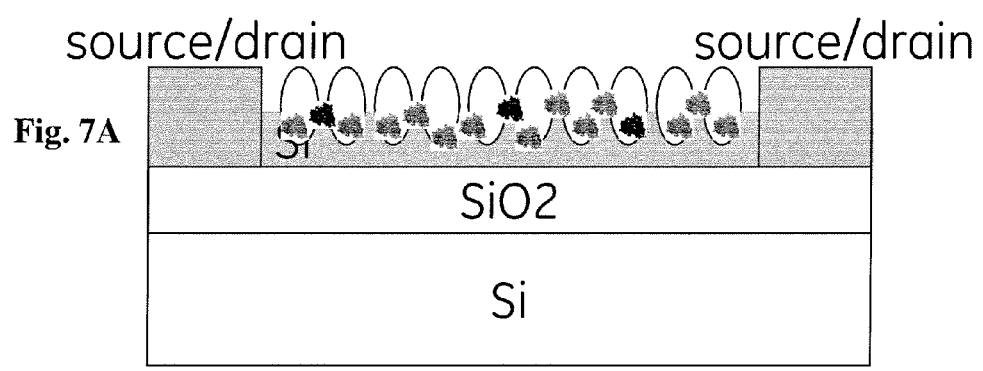
FIGS. 7A-7B illustrate embodiments of a channel of a substrate with partial nanopores located therein.
Figure 7B:
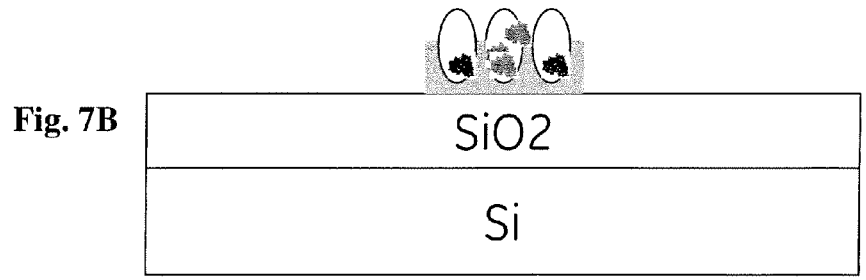

FIGS. 7A and 7B illustrate embodiments of the present disclosure with partially etched nanopores fabricated on a channel of an underlying substrate layer. The nanopore diameter is approximately 10-20 nm. The channel width is greater or equal to 50 nm with a channel thickness of greater than or equal to 10 nm.

Figure 8:
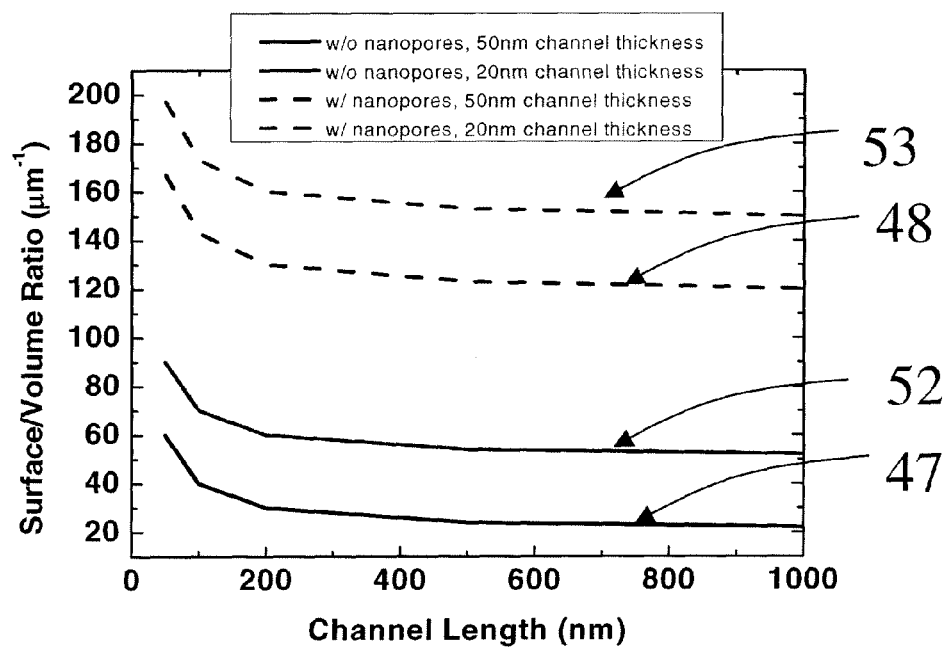
FIG. 8 is a diagram of the Surface/Volume ratio vs. Channel Length for channels shown in FIGS. 7A and 7B, with and without partial nanopores, where the channel width is approximately 20 nm or 50 nm.

FIG. 8 is a graph of the embodiments shown in FIGS. 7A and 7B illustrating the difference between channels with 20 nm thickness and channels with 50 nm thicknesses with and without nanopores. As seen in line 47 a channel with a 50 nm thickness without nanopores decreases in surface/volume ratio from 60 $\mu m^{-1}$ about 22 $\mu m^{-1}$ while, as seen in line 48, the same channel with the same thickness of 50 nm channels with nanopores has surface/volume ratio of approximately 170 $\mu m^{-1}$ at 100 nm channel length that decreases only to about 120 $\mu m^{-1}$ for channel length of nearly 1000 nm.

Similarly FIG. 8 shows, in line 52, that a channel with 20 nm thickness without nanopores that the surface-to-volume ratio drops from about 90 $\mu m^{-1}$ at a channel width of about 50 nm to a surface-to-volume ratio of about 52 $\mu m^{-1}$ for a channel width of about 1000 nm. Comparatively, as seen in line 53, a channel with the same 20 nm thickness with nanopores decreases surface-to-volume from about 200 $\mu m^{-1}$ to 160 $\mu m^{-1}$ for a channel length of 1000 nm. This illustrates that the present disclosure provides that partially formed nanopores on the substrate layer also provide for increased surface-to-volume ratio and achieve high sensitivity for larger channel length.

Figure 9:
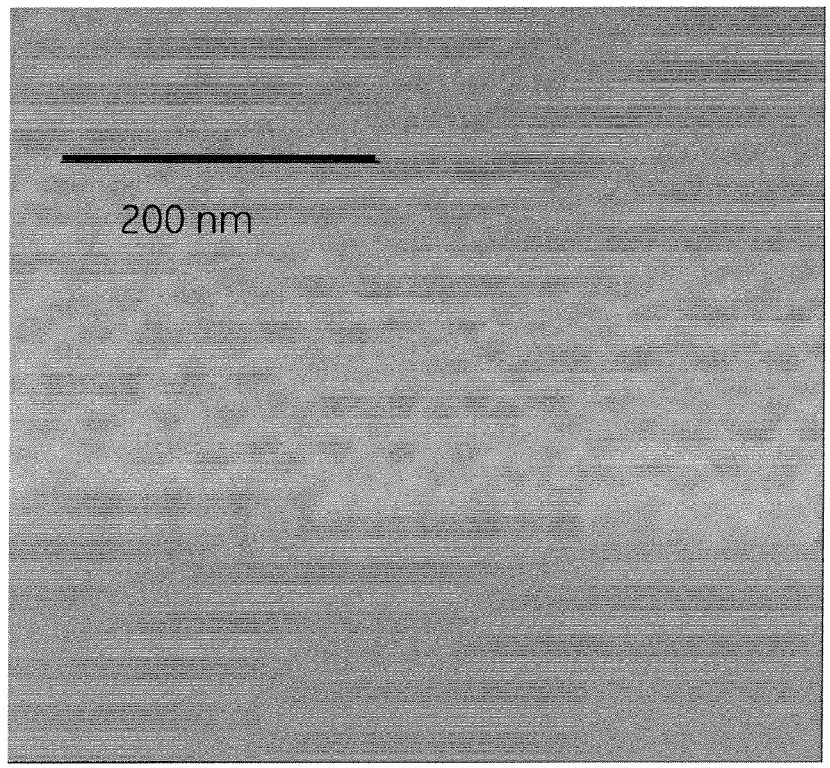
FIG. 9 is a photograph of an embodiment of the nanopores with a diameter that is approximately 15 nm.

FIG. 9 is a photograph showing nanopores in a Si layer on a substrate in accordance with the present disclosure having a diameter of about 15 nm. The scale shown is 200 nm.

In another aspect, the present disclosure provides a method for making a biosensing device. The method comprises providing a substrate layer, an insulating layer and a semiconducting layer. FIG. 10A-10I illustrate the fabrication of the device in accordance with the teachings of the present disclosure. The device fabrication starts with a silicon-on-insulator (SOI) structure 64 (FIG. 10A). The SOI wafer with different top Si layer thickness may be purchased from a commercial source (SOITEC in France, for example). Optionally, the top Si layer 65 may be thinned by thermal oxidation and followed by a wet etch (buffered oxide etch) to remove converted SiO2. The nanopores in device channel (top Si layer) may be formed by block copolymer nanolithography, or by other nanopatterning techniques (nanoimprint, soft lithography, or e-beam lithography, etc.).

The block copolymer (BCP) 68 may be spun on the SOI wafer 64 (FIG. 10B). Exemplary block copolymers useful in the invention include, but not limited to, polystyrene-polybutadiene (PS-PB), postyrene-polyisoprene (PS-PB), polystyrene-b-poly(methyl methacrylate) (PS-b-PMMA), and the like. Block copolymers are composed of two different polymer chains covalently bonded together on one end. Polymers are usually immiscible with one another and phase-separate; in block copolymers, molecular connectivity forces phase separation to occur on molecular-length scales. As a result, periodically ordered nanometer-sized microdomains (such as cylinders or spheres) form, and their specific chemical, electrical, optical, or mechanical properties can be controlled by the choice of the constituent polymers. The sizes and periods of these microdomain structures are governed by the chain dimensions and are typically on the order of 10-30 nm. Structures smaller than 10 nm are also obtainable if one chooses appropriate blocks with a high Flory-Huggins interaction parameter and decreases the block lengths.

For example, asymmetric polystyrene-polybutadiene (PS-PB) diblock copolymer in toluene solution can be spin-coated onto the SOI wafer and film thickness is controlled by varying spinning speed and polymer concentration (FIG. 10C). In bulk, the PS-PI separates into a spherical morphology and produces 70 (PI spheres) in 69 (PS matrix) with body-centered-cubic order. The films are then annealed at 125° C., a temperature above their glass transition temperatures, for 24 hours in vacuum to obtain well-ordered morphologies. The microdomain monolayer film was exposed to ozone to selectively degrade and remove the PB spherical domains before a $CF_4$ reactive ion etch (RIE) or $CF_4/O_2$ RIE. Ozone predominantly attacks the carbon-carbon double bonds in the PB backbone, cutting the bonds and producing PB fragments that can be dispersed in water. This results in regular spherical voids in the PS matrix and hence in a variation of the effective total thickness of the copolymer mask. The regions underneath the empty spheres are exposed to the RIE to produce holes in silicon, whereas the rest is still protected. Chlorine-based or fluorine-based reactive ion etching (RIE) is used to etch Si, with the copolymer film itself as the etching mask (FIG. 10D). Etching may be effected by several other techniques known in the art, such as electron cyclotron resonance (ECR) high density plasma etch or inductively coupled plasma (ICP) etch, chemically assisted ion beam etching (CAIBE), wet chemical etch, and the like. The depth of this Si etch may be controlled by controlling etch time with a fixed etch rate, to achieve either complete etch or incomplete etch.

After Si is completely removed from the nanopores and the underlying SiO2 is exposed, an optional thin layer of thin metal, such as Au or Ag, may be deposited on SiO2 surface 66 in the nanopores by e-beam evaporation, thermal evaporation, sputtering, or other metal deposition techniques. The remaining BCP may be removed by oxygen plasma, or by solvents (acetone, etc.), or other strippers (FIG. 10-E). The device active region (device channel) is patterned by conventional photolithography for channel width greater than 300 nm or nanopatterning techniques for channel width less that 300 nm, and then etched by a plasma etch or wet chemical etch (FIG. 10F).

For the complete etch where Si is completely removed inside nanopores, a silane layer can be selectively formed on bottom SiO2 but not on Si surface or on Au surface but not on Si or SiO2 surface FIG. 10G), and antibody or other receptor ligands can be immobilized on silanized surface (FIG. 10H). In another embodiment, a Si—C functionalization may be formed on Si surface and then antibody or other receptor ligands is attached. For the incomplete etch where Si is partially removed inside nanopores, the surface can be modified and functionalized with antibodies or other receptor ligands. This arrangement physically moves the binding sites close to the sensing surface. Proteins or other biomolecules complementary to the receptor ligands can then bind on the receptor ligands and thus change conduction of the device channel (FIG. 10I).

The density of nanopores can be controlled by manipulating the composition of the block copolymers. For example, density of nanopores can be controlled between $10^{10}$~$10^{12}$ $cm^{-2}$, or preferably $4\times10^{10}$ to $2\times10^{11}$ $cm^{-2}$ corresponding to pitches of nanopores between 20 nm to 50 nm. The presence of nanopores increases surface-to-volume of the device channel, and therefore increase signal-to-noise ratio when binding events modulate conductance of the device channel.

The biosensing device measures the variation in its conductance due to the variation of the surface potential. In one embodiment, a reference device without antibody or other receptor molecules may be positioned close to the sensing device. The response from the reference device may be subtracted from the sensing device to account for non-specific binding. Other components that may be used in the biosensing may include membranes to filter particulate matter, a buffer solution, and so on.

In another aspect, the present disclosure provides a method for analyzing analytes in solution using the biosensing device described herein. The present disclosure also provides kits that comprise biosensing device described herein.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A biosensing FET device having a sensing surface, comprising:
   a semiconductor layer comprising one or more channels having one or more nanopores in the channel, wherein the nanopores comprise a biomolecule;
   an insulator layer;
   an underlying substrate layer; and wherein the biosensing FET device is adapted to operate in solutions having an ionic strength that is equal to or less than 200 mM.

2. The biosensing device of claim 1, wherein one or more of said channels has a height and one or more of said nanopores has a depth that is less than the height of one or more of said channels.

3. The biosensing device of claim 1, wherein one or more of the channels has a height, and wherein one or more of the nanopores in the channels has a depth that is the same as the height of one or more of the channels.

4. The biosensing device of claim 3, wherein the nanopores have a depth that is greater than the height of one or more of the channels so that the nanopores extend through the top surface of, and partially into, the insulator layer, and wherein the nanopores have an inside surface, at least a portion of which is functionalized, that is partially in the semiconductor layer and partially in the insulator layer.

5. The biosensing device of claim 4, wherein the nanopores are functionalized, at least in part, with one or more binders.

6. The biosensing device of claim 1, wherein one or more of the nanopores is functionalized, at least in part, with one or more binders.

7. The biosensing device of claim 1 wherein the nanopores in the channel of the semiconductor layer locate one or more binding sites proximate the sensing surface.

8. The biosensing device of claim 7, is adapted to operate in solutions having an ionic strength that is equal to or less than 10 mM, and wherein the nanopores locate one or more of the binding sites less than or equal to 5 nm from the sensing surface.

9. The biosensing device of claim 7, wherein the nanopores locate the binding sites less than or equal to 1 nm from the sensing surface.

10. The biosensing device of claim 1, wherein the channels have a density of nanopores that is between $10^{10}$ to $10^{12}$ per $cm^{-2}$.

11. The biosensing device of claim 1, wherein the semiconductor layer comprises silicon.

12. A biodetector comprising the biosensing device of claim 1.

* * * * *